United States Patent [19]

Stark et al.

[11] Patent Number: 5,128,361
[45] Date of Patent: Jul. 7, 1992

[54] IMIDAZOLINE DERIVATIVES FOR SYSTEMIC COMBATING OF ECTOPARASITES IN HOST ANIMALS

[75] Inventors: Herbert Stark, Kelkheim; Gerhard Salbeck, Kriftel; Werner Bonin, Kelkheim, all of Fed. Rep. of Germany

[73] Assignee: Hoechst Aktiengesellschaft, Frankfurt am Main, Fed. Rep. of Germany

[21] Appl. No.: 452,799

[22] Filed: Dec. 18, 1989

[30] Foreign Application Priority Data

Dec. 20, 1988 [DE] Fed. Rep. of Germany ....... 3842798

[51] Int. Cl.$^5$ ........................................ A61K 31/415
[52] U.S. Cl. ..................................... 514/401; 548/353
[58] Field of Search ..................... 548/353; 514/401

[56] References Cited

U.S. PATENT DOCUMENTS

| | | | |
|---|---|---|---|
| 4,226,876 | 10/1980 | Copp et al. ................... | 424/273 |
| 4,254,133 | 3/1981 | Kristinsson et al. ........... | 424/273 |
| 4,414,223 | 11/1983 | Copp et al. ................... | 424/273 |

FOREIGN PATENT DOCUMENTS

| | | | |
|---|---|---|---|
| 506440 | 2/1976 | Australia . | |
| 35464/78 | 4/1978 | Australia . | |
| 0086043 | 1/1982 | European Pat. Off. ............ | 548/353 |
| 0049797 | 10/1980 | Fed. Rep. of Germany ...... | 514/400 |
| 1180862 | 2/1970 | United Kingdom . | |

OTHER PUBLICATIONS

Morrison and Boyd, "Organic Chemistry", 3rd Ed. Allyn and Bacon, Inc., Boston, 1973, p. 742.

*Primary Examiner*—Patricia L. Morris
*Assistant Examiner*—Lenora Miltenberger
*Attorney, Agent, or Firm*—Curtis, Morris & Safford

[57] ABSTRACT

The present invention relates to agents for systemic combating of ectoperasites in host animals, containing a compound of the formul I (I)

in which $R^1$ denotes hydrogen, $(C_1-C_5)$-alkyl, $(C_1-C_3)$-halogenoalkyl or halogen;

$R^2$ and $R^3$ independently of one another denote $(c_1-C_5)$-alkyl, $(C_2-C_5)$-alkenyl, $(C_2-C_5)$-alkynyl, $(C_3-C_7)$-cycloalkyl, $(C_3-C_7)$-cycloalkenyl, $(C_1-C_3)$-halogenoalkyl, halogen, cyano, nitro, $(C_1-C_5)$-alkoxy, $(C_1-C_3)$-alkoxy-$C_1-C_3)$-alkyl, $(C_1-C_3)$-halogenoalkoxy or $(C_1-C_3)$-alkylthio, or $R^2$ and $R^3$ together form a polymethylene chain having 2 to 5 carbon atoms:

$R^4$ denotes hydrogen, $(c_1-C_{10})$-alkyl, $(C_2-C_5)$-alkenyl or $(C_3-C_7)$-cycloalkyl;

$R^5$ denotes hydrogen, $(C_1-C_{10})$-alkyl, $(C_3-C_5)$-alkenyl, $C_3-C_5)$-alkynyl, $(C_3-C_7)$-cycloalkyl, $(C_3-C_7)$-cycloalkenyl, $(C_1-C_3)$-halogenoalkyl or $(C_1-C_3)$-alkoxy-(C hd 1–$C_3$)-alkyl;

X denotes oxygen, sulfur or an —$NR^6$—group; and $R^6$ denotes hydrogen, $(C_1-C_5)$-alkyl, $(C_3-C_5)$-alkenyl, $C_3-C_5)$-alkynyl, $(C_3-C_7)$-cycloalkyl, $C_3-C_7)$-cycloalkenyl, $(C_1-C_3)$-halogenoalkyl or $(C_1-C_3)$-alkoxy-$(C_1-C_3)$-alkyl, or biologically tolerated acid addition salts thereof.

The compounds of the formulas I are novel in some cases and are likewise included in the invention.

2 Claims, No Drawings

IMIDAZOLINE DERIVATIVES FOR SYSTEMIC COMBATING OF ECTOPARASITES IN HOST ANIMALS

DESCRIPTION

Imidazoline derivatives of the following formula I are known in some cases and their insecticidal or acaricidal activity has been previously described (AU-PS 506,440 and DE-OS 2,750,902, 2,756,638 and 2,818,367).

However, the methods described in these specifications for combating pests are always based on the fact that the pests are sprayed with an agent containing the active compound or, in the case of ectoparasites, are immersed in this agent, that is to say the pests brought into contact in some form externally with corresponding agent. This also corresponds to customary combating of ectoparasites in practice, where affected host animals are sprayed, dipped in baths or treated with pour-on solutions.

It has now been found, surprisingly, compounds of the formula I are advantageously suitable for systemic combating of ectoparasites in host. The present invention thus relates to agents for systemic combating of ectoparasites in host animals, contain a compound of the formula I

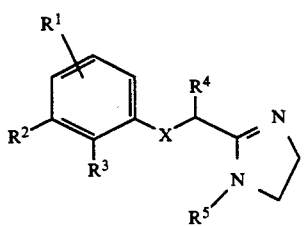 (I)

in which
  $R^1$ denotes hydrogen, $(C_1-C_5)$-alkyl, $(C_1-C_3)$-halogenoalkyl or halogen;
  $R^2$ and $R^3$ independently of one another denote $(C_1-C_5)$-alkyl, $(C_2-C_5)$-alkenyl, $(C_2-C_5)$-alkynyl, $(C_3-C_7)$-cycloalkyl, $(C_3-C_7)$-cycloalkenyl, $(C_1-C_3)$-halogenoalkyl, halogen, cyano, nitro, $(C_1-C_5)$-alkoxy, $(C_1-C_3)$-alkoxy-$(C_1-C_3)$-alkyl, $(C_1-C_3)$-halogenoalkoxy or $(C_1-C_3)$-alkylthio, or $R^2$ and $R^3$ together form a polymethylene chain having 2 to 5 carbon atoms;
  $R^4$ denotes hydrogen, $(C_1-C_{10})$-alkyl, $(C_2-C_5)$-alkenyl or $(C_3-C_7)$-cycloalkyl;
  $R^5$ denotes hydrogen, $(C_1-C_{10})$-alkyl, $(C_3-C_5)$-alkenyl, $(C_3-C_5)$-alkynyl, $(C_3-C_7)$-cycloalkyl, $C_3-C_7$-cycloalkenyl, $(C_1-C_3)$-halogenoalkyl or $(C_1-C_3)$-alkoxy-$(C_1-C_3)$-alkyl;
  X denotes oxygen, sulfur or an $-NR^6-$ group; and
  $R^6$ denotes hydrogen, $(C_1-C_5)$-alkyl,$(C_3-C_5)$-alkenyl, $(C_3-C_5)$-alkynyl, $(C_3-C_7)$-cycloalkyl, $(C_3-C_7)$-cycloalkenyl, $(C_1-C_3)$-halogenoalkyl or $(C_1-C_3)$-alkoxy-$(C_1-C_3)$-alkyl,
or biologically tolerated acid addition salts thereof.

Alkyl here denotes either straight-chain or branched alkyl, and halogen preferably denotes F or Cl. Preferred biologically tolerated acid addition salts of the compounds I are the hydrohalides, in particular the hydrochlorides. The agents according to the invention can also contain several active compounds I.

The compounds according to the invention can also be advantageously used for simultaneous combating of endoand ectoparasites in combination with preparations having a systemic action, such as, for example, the avermectins or with levamisol or netobimin, or, in the case of oral administration, in combination with preparations from the group of benzimidazoles, such as, for example, phenbendazole or albendazole. Preferred compounds of the formula I are those in which
  $R^1$ denotes hydrogen, $(C_1-C_3)$-alkyl, $(C_1-C_3)$-halogenoalkyl, F or Cl;
  $R^2$ and $R^3$ independently of one another denote $(C_1-C_3)$-alkyl, $(C_2-C_3)$-alkenyl, $(C_2-C_3)$-alkynyl, $(C_3-C_5)$-cycloalkyl, $(C_1-C_3)$-halogenoalkyl, halogen, cyano, nitro, $(C_1-C_3)$-alkoxy, $(C_1-C_3)$-alkoxy-$(C_1-C_2)$-alkyl, $(C_1-C_3)$-halogenoalkoxy or $(C_1-C_3)$-alkylthio, or $R^2$ and $R^3$ together form a polymethylene chain having 2 to 5 carbon atoms;
  $R^4$ denotes hydrogen, $(C_1-C_4)$-alkyl, $(C_2-C_3)$-alkenyl or $(C_3-C_6)$-cycloalkyl;
  $R^5$ denotes hydrogen, $(C_1-C_4)$-alkyl, $(C_3-C_4)$-alkenyl, $(C_3-C_4)$-alkynyl, $(C_3-C_6)$-cycloalkyl, $(C_3-C_5)$-cycloalkenyl, $(C_1-C_3)$-halogenoalkyl or $(C_1-C_3)$-alkoxy-$(C_1-C_2)$-alkyl;
  X denotes oxygen or an $-NR^6-$ group; and
  $R^6$ denotes hydrogen, $(C_1-C_4)$-alkyl,$(C_3-C_4)$-alkenyl, $(C_3-C_4)$-alkynyl, $(C_3-C_6)$-cycloalkyl, $(C_1-C_3)$-halogenoalkyl or $(C_1-C_3)$-alkoxy-$(C_1-C_2)$-alkyl,
and biologically tolerated acid addition salts thereof.

These acid addition salts are the main use form of the compounds I.

The hydrohalides nos. 1-115 below may be mentioned in particular:
1. 2-(2,5-dichloro-3-trifluoromethylphenylaminomethyl)-2-imidazoline hydrochloride
2. 2-(2,6-dichloro-3-methylphenyl-aminomethyl)-2-imidazoline hydrochloride
3. 2-(6-fluoro-2,3-dimethylphenyl-aminomethyl)-2-imidazoline hydrochloride
4. 2-(2-chloro-4-fluoro-3-methylphenyl-aminomethyl)-2-imidazoline hydrochloride
5. 2-(2-chloro-4-fluoro-3-trifluoromethylphenyl-aminomethyl)-2-imidazoline hydrochloride
6. 2-(2,4-dichloro-3-fluorophenyl-aminomethyl)-2-imidazoline hydrochloride
7. 2-(4-methoxy-2,3-dimethylphenyl-aminomethyl)-2-imidazoline hydrochloride
8. 2-(2,3,4-trimethylphenyl-aminomethyl)-2-imidazoline hydrochloride
9. 1-ethyl-2-(6-fluoro-2,3-dimethylph-enyl-aminomethyl)-2-imidazoline hydrochloride
10. 2-(2-methyl-3-vinylphenyl-aminomethyl)-2-imidazoline hydrochloride
11. 2-(2-methyl-3-allylphenyl-aminomethyl)-2-imidazoline hydrochloride
12. 1-methyl-2-(2-allyl-3-methylphenyl-aminomethyl)-2-imidazoline hydrochloride
13. 2-(3-ethynyl-2-methylphenyl-aminomethyl)-2-imidazoline hydrochloride
14. 2-(2-cyclopropyl-3-methylphenyl-aminomethyl)-2-imidazoline hydrochloride
15. 2-(2-chloro-3-cyclopentyl-2-methylphenyl-aminomethyl)-2imidazoline hydrochloride
16. 2-(3-cyclopentyl-2-methylphenyl-aminomethyl)-2-imidazoline hydrochloride
17. 2-(3-cyclopent-1-ene-2-methylphenyl-aminomethyl)-2-imidazoline hydrochloride
18. 2-(3-trifluoromethyl-2-methylphenyl-aminomethyl)-2-imidazoline hydrochloride 19. 2-(3-nitro-2-methylphenyl-aminomethyl)-2-imidazoline hydrochloride
20. 2-(3-nitro-2-chlorophenyl-aminomethyl)-2-imidazoline hydrochloride
21. 2-(2-nitro-3-methylphenyl-aminomethyl)-2-imidazoline hydrochloride
22. 2-(3-methoxymethyl-2-methylphenyl-aminomethyl)-2-imidazoline hydrochloride
23. 1-ethyl-2-(3-methoxymethyl-2-methylphenyl-aminomethyl)-2-imidazoline hydrochloride
24. 2-(3-chloro-2-difluoromethoxyphenyl-aminomethvl-)-2-imidazoline hydrochloride
25. 2-(3-difluoromethoxy-2-methylphenyl-aminomethyl)-2-imidazoline hydrochloride
26. 2-(2-chloro-3-tetrafluoroethoxy-phenyl-aminomethyl)-2-imidazoline hydrochloride
27. 2-(2-methyl-3-methylthiophenyl-aminomethyl)-2-imidazoline hydrochloride
28. 2-((1,2,3,4-tetrahydronaphth-5-yl)-aminomethyl)-2-imidazoline hydrochloride
29. 2-(indan-4-yl-aminomethyl)-2-imidazoline hydrochloride
30. 2-(3-allyl-2-methylphenoxy-methyl)-2-imidazoline hydrochloride
31. 2-(3-cyclopropyl-2-methylphenoxy-methyl)-2-imidazoline hydrochloride
32. 2-(3-trifluoromethyl-2-methylphenoxy-methvl)-2-imidazoline hydrochloride
33. 2-(2-cyano-3-methylphenoxy-methyl)-2-imidazoline hydrochloride
34. 2-(3-methoxymethyl-2-methylphenoxy-methyl)-2-imidazoline hydrochloride
35. 2-(3-difluoromethoxy-2-methylphenoxy-methvl)-2-imidazoline hydrochloride
36. 2-(2-ethyl-3-methylphenyl-aminomethyl)-2-imidazoline hydrochloride
37. 2-(2,3-diethylphenyl-aminomethyl)-2-imidazoline hydrochloride
38. 2-(3-ethyl-2-methylphenyl-aminomethyl-)-2-imidazoline hydrochloride
39. 2-(3-fluoro-2-methylphenyl-aminomethyl)-2-imidazoline hydrochloride
40. 2-(3-bromo-2-methylphenyl-aminomethyl)-2-imidazoline hydrochloride
41. 2-(3-chloro-2-fluorophenyl-aminomethyl)-2-imidazoline hydrochloride
42. 2-(3-nitro-2-methylphenoxy-methyl)-2-imidazoline hydrochloride
43. 2-(3-ethyl-2-methyl-phenoxy-methyl)-2-imidazoline hydrochloride
44. 2-(3-fluoro-2-methylphenoxy-methyl)-2-imidazoline hydrochloride
45. 2-(3-bromo-2-methylphenoxy-methyl)-2-imidazoline hydrochloride
46. 2-(3-chloro-2-fluorophenoxy-methyl)-2-imidazoline hydrochloride
47. 2-(1-(2,3-dimethylphenyl-amino)-prop-2-enyl)-2-imidazoline hydrochloride
48. 2-(cyclopropyl-(2,3-dimethylphenyl-amino)-methyl)-2-imidazoline hydrochloride
49. 2-(1-(2,3-dimethylphenyl-amino)-ethyl)-2-imidazoline hydrochloride
50. 2-(1-(2,3-dimethylphenyl-N-methyl-amino)-ethyl)-2-imidazoline hydrochloride
51. 1-methyl-2(1-(2,3-dimethylphenyl-amino)-ethyl)-2-imidazoline hydrochloride
52. 1-ethyl-2-(1-(2,3-dimethylphenyl-amino)-ethyl)-2-imidazoline hydrochloride
53. 1-methyl-2-(1-(2,3-dimethylphenyl-N-methyl-amino)-ethyl)-2-imidazoline hydrochloride
54. 1-ethyl-2-(1-(2,3-dimethylphenyl-N-methyl-amino)-ethyl)-2-imidazoline hydrochloride
55. 2-(2,3-dimethylphenyl-thiomethyl)-2-imidazoline hydrochloride
56. 2-(3-chloro-2-methylphenyl-thiomethyl)-2-imidazoline hydrochloride
57. 2-(2-chloro-3-methylphenyl-thiomethyl)-2-imidazoline hydrochloride
58. 1-ethyl-2-(3-chloro-2-methylph-enyl-thiomethyl)-2-imidazoline hydrochloride
59. 2-(1-(2,3-dimethylphenyl-thio)-ethyl)-2-imidazoline hydrochloride
60. 1-ethyl-2-(2,3-dimethylphen-yl-aminomethyl)-2-imidazoline hydrochloride
61. 1-ethyl-2-(2,3-dimethylphenyl-aminomethyl)-2-imidazoline hydrochloride
62. 1-n-propyl-2-(2,3-dimethylphen-yl-aminomethyl)-2-imidazoline hydrochloride
63. 1-iso-propyl-2-(2,3-dimethylphenyl-aminomethyl)-2-imidazoline hydrochloride
64. 1-ethyl-2-(2-chloro-3-methylphenyl-aminomethyl)-2-imidazoline hydrochloride
65. 1-ethyl-2-(3-chloro-2-methylphenyl-aminomethyl)-2-imidazoline hydrochloride
66. 1-ethyl-2-(2,3-dichlorophenyl-aminomethyl)-2-imidazoline hydrochloride
67. 1-allyl-2-(2,3-dimethylphenyl-aminomethyl)-2-imidazoline hydrochloride
68. 1-but-2-enyl-2-(2,3-dimethylphenyl-aminomethyl)-2-imidazoline hydrochloride
69. 1-propargyl-2-(2,3-dimethylphenyl-aminomethyl)-2-imidazoline hydrochloride
70. 1-cyclopropyl-2-(2,3-dimethylphenyl-aminomethyl)-2-imidazoline hydrochloride
71. 1-cyclohexyl-2-(2,3-dimethylphenyl-aminomethyl)-2-imidazoline hydrochloride
72. 1-cyclopent-2-enyl-2-(2,3-dimethylphenyl-aminomethyl)-2-imidazoline hydrochloride
73. 1-(2,2,2-trifluoroethyl)-2-(2,3-dimethylphenylaminomethyl)-2-imidazoline hydrochloride
74. 1-(2-methoxyethyl)-2-(2,3-dimethylphenyl-aminomethyl)-2-imidazoline hydrochloride
75. 1-allyl-2-(2,3-dimethylphenoxy-methyl)-2-imidazoline hydrochloride
76. 1-propargyl-2-(2,3-dimethylphenoxy-methyl)-2-imidazoline hydrochloride
77. 1-cyclopropyl-2-(2,3-dimethylphenoxy-methyl)-2-imidazoline hydrochloride
78. 1-cyclopentyl-2-(2,3-dimethylphenox-y-methyl)-2-imidazoline hydrochloride
79. 1-cyclopent-2-ene-2-(2,3-dimethylphenoxy-methyl)-2-imidazoline hydrochloride
80. 1-(2,2,2-trifluoroethyl-)-2-(2,3-dimethylphenoxymethyl)-2-imidazoline hydrochloride
81. 1-(2-methoxyethyl)-2-(2,3-dimethylphenoxymethyl)-2-imidazoline hydrochloride
82. 2-(2,3-dimethylphenyl-N-ethyl-aminomethyl)-2-imidazoline hydrochloride
83. 2-(2,3-dimethylphenyl-N-n-propyl-aminomethyl)-2-imidazoline hydrochloride
84. 2-(2,3-dimethylphenyl-N-iso-propyl-aminomethyl)-2-imidazoline hydrochloride
85. 2-(2,3dimethylphenyl-N-butyl-aminomethyl)-2-imidazoline hydrochloride
86. 2-(2,3-dimethylphenyl-N-allyl-aminomethyl)-2-imidazoline hydrochloride 87. 2-(2,3-dimethylphenyl-N-propargyl-aminomethyl)-2-imidazoline hydrochloride
88. 2-(2,3-dimethylphenyl-N-cyclopropyl-aminomethyl)-2-imidazoline hydrochloride
89. 2-(2,3-dimethylphenyl-N-cyclopent-2-enyl-aminomethyl)-2-imidazoline hydrochloride
90. 2-(2,3-dimethylphenyl-N-(2,2,2-trifluoroethyl)-aminomethyl)-2-imidazoline hydrochloride
91. 2-(2,3-dimethylphenyl-N-(2-methoxyethyl)-aminomethyl)-2-imidazoline hydrochloride
92. 1-ethyl-2-(2,3-dimethylphenyl-N-methyl-aminomethyl)-2-imidazoline hydrochloride
93. 1-ethyl-2-(2-chloro-3-methylphenyl-N-methyl-aminomethyl)-2-imidazoline hydrochloride
94. 1-ethyl-2-(3-chloro-2-methylphenyl-N-methyl-aminomethyl)-2-imidazoline hydrochloride
95. 1-ethyl-2-(2,3-dichlorophenyl-N-methyl-aminomethyl)2-imidazoline hydrochloride
96. 1-ethyl-2-(2,3-dimethylphenyl-N-ethyl-aminomethyl)2-imidazoline hydrochloride
97. 2-(2,3,6-trimethylphenyl-aminomethyl)-2-imidazoline hydrochloride
98. 2-(2,3-dimethylphenyl-aminomethyl)-2-imidazoline hydrochloride
99. 2-(2-chloro-3-methyl-phenyl-aminomethyl)-2-imidazoline hydrochloride
100. 2-(3-chloro-2-methylphenyl-aminomethyl)-2-imidazoline hydrochloride
101. 2-(2,3-dichlorophenyl-aminomethyl)-2-imidazoline hydrochloride
102. 1-methyl-2-(2,3-dimethylphenyl-aminomethyl)-2-imidazoline hydriodide
103. 2-(2,3-dimethylphenyl-N-methyl-aminomethyl)-2-imidazoline hydrochloride
104. 2-(2-chloro-3-methylphenyl-N-methyl-aminomethyl)-2-imidazoline hydrochloride
105. 2-(3-chloro-2-methylphenyl-N-methyl-aminomethyl)-2-imidazoline hydrochloride
106. 2-(2,3-dichlorophenyl-N-methyl-aminomethyl)-2-imidazoline hydrochloride
107. 1-methyl-2-(2,3-dimethylphenyl-N-methyl-aminomethyl)-2-imidazoline hydrochloride
108. 2-(2,3-dimethylphenoxy-methyl)-2-imidazoline hydrochloride
109. 2-(2-chloro-3-methylphenoxy-methyl)-2-imidazoline hydrochloride
110. 2-(3-chloro-2-methylphenoxy-methyl)-2-imidazoline hydrochloride
111. 2-(1-(2,3-dimethylphenoxy)-ethyl)-2-imidazoline hydrochloride
112. 2-(1-(2,3-dimethylphenoxy)-propyl)-2-imidazoline hydrochloride
113. 1-methyl-2-(2,3-dimethylphenoxymethyl)-2-imidazoline hydrochloride
114. 1-ethyl-2-(2,3-dimethylphenoxy-methyl)-2-imidazoline hydrochloride
115. 1-methyl-2-(1-(2,3-dimethylphenoxy)-ethyl)-2-imidazoline hydrochloride When agents are used systemically on the host animal for combating ectoparasites, in addition to a good activity a good tolerability in the host animal organism is also required. A whole series of imidazolines which have an influence on the cardiovascular system of mammals is described in the literature (for example GB-PS 1,174,349), amongst others also those which fall under the claim of the general formula I. This undesirable side effect limits the dose in the use according to the invention of agents which contain compounds of the general formula I. The effective dose for combating ectoparasites and the dose tolerated in the treated host animal are often close to one another. It is therefore surprising and was not to be predicted that compounds of the general formula I in which $R^5$ is not hydrogen have a significantly better therapeutic index than compounds where $R^5$ is hydrogen.

The compounds 9, 51, 52, 54, 60, 61, 62, 64, 65, 67, 70, 73, 74, 92, 93 and 94, other biologically tolerated acid addition salts thereof (not hydrochlorides) and the particular free base are therefore particularly preferred.

The compounds of the formula I are novel in some cases. The present invention thus also relates to the compounds of the formula Ia

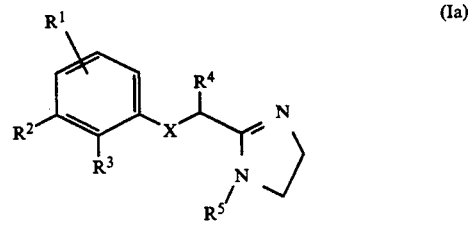

in which
$R^2$, $R^3$, $R^4$, $R^5$ and $R^6$ have the meaning described under formula I, if X represents —$NR^6$— and $R^1$ is not hydrogen and is not 6-$CH_3$;

$R^2$, $R^3$, $R^4$, $R^5$ and $R^6$ have the meaning described under formula I, if X represents oxygen and $R^1$ is not hydrogen and is not chlorine or $CH_3$;

$R^1$, $R^4$, $R^5$ and $R^6$ have the meaning described under formula I, if X is —$NR^6$— and $R^2$ and $R^3$ represent ($C_2$–$C_5$)-alkenyl, ($C_2$–$C_5$)-alkynyl, ($C_3$–$C_7$)-cycloalkyl, ($C_3$–$C_7$)-cycloalkenyl, ($C_1$–$C_3$)-halogenoalkyl, nitro, ($C_1$–$C_3$)-alkoxy-($C_1$–$C_3$)-alkyl, ($C_1$–$C_3$)-halogenoalkoxy or ($C_1$–$C_3$)-alkylthio or together form a polymethylene chain having 2 to 5 carbon atoms;

$R^1$, $R^4$, $R^5$ and $R^6$ have the meaning described under formula I, if X is oxygen and $R^2$ and $R^3$ represent ($C_2$–$C_5$)-alkenyl, ($C_2$–$C_5$)-alkynyl, ($C_3$–$C_7$)-cycloalkyl, ($C_3$–$C_7$)-cycloalkenyl, ($C_1$–$C_3$)-halogenoalkyl, cyano, ($C_1$–$C_3$)-alkoxy-($C_1$–$C_3$)-alkyl, ($C_1$–$C_3$)-halogenoalkoxy or ($C_1$–$C_3$)-alkylthio;

$R^1$, $R^4$, $R^5$ and $R^6$ have the meaning described under formula I, if X represents —$NR^6$— and at least one of the radicals $R^2$ or $R^3$ is not methyl, chlorine, cyano or ($C_1$–$C_5$)-alkoxy;

$R^1$, $R^4$, $R^5$ and $R^6$ have the meaning described under formula I, if X represents oxygen and at least one of the radicals $R^2$ or $R^3$ is not methyl, iso-propyl, chlorine, nitro or ($C_1$–$C_5$)-alkoxy, or $R^2$ and $R^3$ together do not form a polymethylene chain having 3 or 4 carbon atoms;

$R^1$, $R^2$, $R^3$, $R^5$, $R^6$ and X have the meaning described under formula I, if $R^4$ represents ($C_2$–$C_5$)-alkenyl or ($C_3$–$C_7$)-cycloalkyl;

$R^1$, $R^2$, $R^3$ and $R^5$ have the meaning described under formula I, if X is —$NR^6$— and $R^6$ is or is not hydrogen and $R^4$ represents ($C_1$–$C_{10}$)-alkyl, ($C_2$–$C_5$)-alkenyl or ($C_3$–$C_7$)-cycloalkyl;

$R^1$, $R^2$, $R^3$, $R^4$ and $R^5$ have the meaning described under formula I, if X represents sulfur;

$R^1$, $R^2$, $R^3$, $R^4$ and $R^6$ have the meaning described under formula I, if X is —$NR^6$— and $R^5$ represents $C_2$— and $C_3$-alkyl, $(C_3-C_5)$-alkenyl, $(C_3-C_5)$-alkynyl, $(C_3-C_7)$-cycloalkyl, $(C_3-C_7)$-cycloalkenyl, $(C_1-C_3)$-halogenoalkyl or $(C_1-C_3)$-alkoxy-$(C_1-C_3)$-alkyl;

$R^1$, $R^2$, $R^3$, $R^4$ and $R^6$ have the meaning described under formula I, if X is oxygen and $R^5$ represents $(C_3-C_5)$-alkenyl, $(C_3-C_5)$-alkynyl, $(C_3-C_7)$-cycloalkyl, $(C_3-C_7)$-cycloalkenyl, $(C_3-C_5)$-halogenoalkyl or $(C_1-C_3)$-alkoxy-$(C_1-C_3)$-alkyl;

$R^1$, $R^2$, $R^3$, $R^4$ and $R^5$ have the meaning described under formula I, if X is —$NR^6$— and $R^6$ represents $(C_2-C_4)$-alkyl, $(C_3-C_5)$-alkenyl, $(C_3-C_5)$-alkynyl, $(C_3-C_7)$-cycloalkyl, $(C_3-C_7)$-cycloalkenyl, $(C_1-C_3)$-halogenoalkyl or $(C_1-C_3)$-alkoxy-$(C_1-C_3)$-alkyl, and biologically tolerated acid addition salts thereof.

Preferred acid addition salts are the hydrohalides, in particular the hydrochlorides. Preferred compounds of the formula Ia are those with example numbers 1 - 96. Of these, the compounds where $R^5$ is not hydrogen. The compounds 9, 51, 52, 54, 60, 61, 62, 64, 65, 67, 70, 73, 74, 92, 93 and 94, other biologically tolerated acid addition salts thereof and the particular free base are thus particularly preferred.

The preparation of the compounds of the formula I is known and is described in detail in the abovementioned prior art. The novel compounds of the formula Ia can be prepared by analogous processes. The present invention thus also relates to a process for the preparation of the compounds of the formula Ia, which comprises a) reacting an aryl compound of the formula II with a chloroalkyl-imidazoline of the formula III, in which the radicals $R^1$ to $R^5$ and X have the meaning specified under formula Ia,

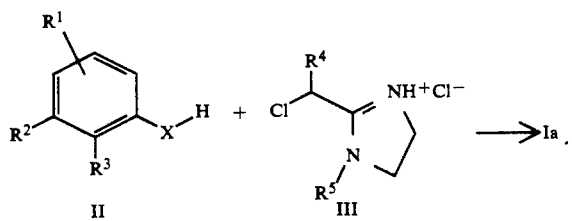

or b) reacting an aryl compound of the general formula V, in which Y is a carboxyl group or a reactive derivative thereof, for example an imidate, thioimidate, ester, orthoester, thioamide, imidohalide or amidine, and the radicals $R^1$ to $R^5$ and X have the meaning specified above, with an ethylenediamine of the formula IV or a salt thereof

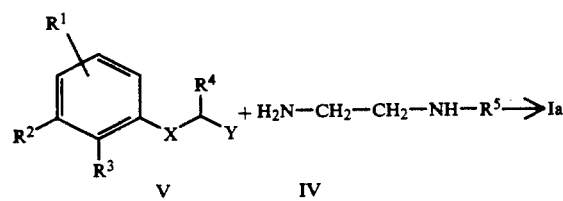

or c) reacting an imidazoline of the general formula VI with an alkyl halide of the general formula $R^5$-Z, in which the radicals $R^1$ to $R^5$ and X have the meaning specified under formula Ia and Z is a halogen atom.

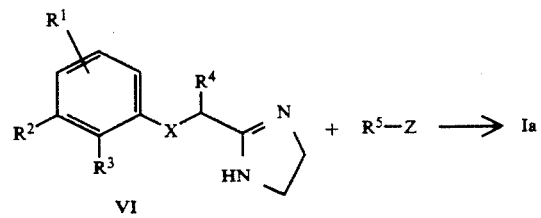

The chloroalkyl-imidazolines of the general formula III can be prepared from 2-chloroalkanoic acid derivatives, for example imide acid esters, and a suitable substituted ethylenediamine of the formula IV (see the literature cited).

The compounds of the general formula Ia can be isolated from the reaction mixture as the free base or in the form of an acid addition salt. The bases can be converted into the acid addition salts by processes which are known per se. For this, the corresponding acid is added to the bases in a solvent. The salts crystallize out of this solution either directly or after addition of a nonpolar solvent or after concentration in vacuo. The salts of the compounds can likewise be converted into the free base or into other acid addition salts For this, either an organic base, for example triethylamine, is added to the salts in a nonpolar solvent and the conjugated acid formed from the base employed is filtered off with suction, the free base of the compounds of the general formula Ia remaining in solution. Or, alternatively, an alkali metal hydroxide is added to an aqueous solution of the salts and the free base of compounds of the general formula Ia is isolated by extraction.

The present invention likewise relates to a method of combating ectoparasites, which comprises administering an agent containing a compound of the formula I parenterally or orally to the host animal. The agent can also consist of only one compound of the formula I or mixtures of these compounds.

When combating ectoparasites systemically in the host animals, a suitable formulation of a compound of the general formula I is administerd to the mammals which usually serve as the host for ectoparasites, such as, for example, sheep, cattle or dogs. As a result, the ectoparasites become detached from the host animal, stop their development or die. If the agents containing the compounds of the general formula I are used prophylactically, infestation of the host animals with ectoparasites is prevented or reduced.

Parasitic arthropods of the Acari class can be combated. The compounds have proven particularly suitable for use on scaled ticks, for example Ixodes spp., Boophilus spp., for example *Boophilus microplus*, Amblyomma spp., Hyalomma spp., Rhipicephalus spp., for example *Rhipicephalus appendiculatus*, Haemaphysalis spp. and Dermacentor spp., and against leather ticks, for example Ornithodorus spp., such as, for example, *Ornithodorus moubata*. Parasitic mites, for example of the genera Sarcoptes, Psoroptes and Chorioptes, can also be combated.

Agents containing the compounds of the general formula I can be administered either parenterally, percutaneously or orally to the host animals. The administration can take place, for example, as a subcutaneous, intravenous, intramuscular or intraperitoneal injection.

In the case of oral use, the agent can be administered either as such or with suitable auxiliaries or diluents or as a mixture with the feed. Particularly preferred methods of administration are subcutaneous injection and oral administration with the feed.

In order to achieve a good long-term action, a compound of the general formula I can be administered several times, or such a compound which has a particularly favorable half-life in the host animal organism can be used, or a depot formulation or an administration system for low-duration dosage of the active compound, such as, for example, an implant or a bolus, can be employed. In practice, a combination of these measures has proven appropriate.

Agents which are employed for topical combating of ectoparasites as a rule contain, in addition to the actual active compound, other auxiliaries and additives as agents which can be used orally or parenterally on mammals. Whereas the former in the composition are amongst the customary formulations for plant protection agents, the latter are pharmaceutical preparations. The invention thus also relates to veterinary pharmaceuticals which contain one or more compounds of the general formula I and which are suitable specifically for oral or parenteral use on vertebrates, in particular in the husbandry of important stock animals, and here specifically on cattle, sheep and pigs, as well as domestic animals, such as dogs and cats.

Compositions which are suitable for oral administration are, for example, powders, tablets, boli, capsules, granules, solutions, suspensions, emulsions or pastes, which contain the active compounds by themselves or together with customary auxiliaries and excipients, such as starch, cellulose powder, talc, magnesium stearate, sugar, gelatin, finely divided silicic acid, carboxymethylcellulose or similar substances. Boli from which compounds of the general formula I are released only slowly, for example in the rumen of cattle, are particularly suitable here for low-duration dosage.

Compositions which are suitable for parenteral administration are, for example, solutions, suspensions and emulsions which are prepared from the active compounds using customary solvents and with the addition of suitable auxiliaries and excipients. Examples of compositions which can be used are aqueous solutions, which contain thickeners if appropriate, such as, for example, polyethylene glycol or carboxymethylcellulose, or oily suspensions, which are prepared using, for example, sesame oil, olive oil or synthetic triglycerides, and if appropriate using surface-active substances, such as sorbitan fatty acid esters. Implant in which compounds of the general formula I are embedded in a biologically degradable matrix are particularly suitable for low-duration dosage by parenteral administration. Such a matrix can be, for example, a starch gel which is softened with glycerin and suitably shaped.

Depot formulations (compare DE-OS 3,521,893 and 3,523,065 and EP-A-0,164,927) are of particular importance for both types of administration.

The active compound concentrations of the compounds I are generally
  a) in feed 100–10,000 ppm, preferably 500–5,000 ppm;
  b) as an injection solution 1–50% by weight, preferably 10–30% by weight; and
  c) as a depot formulation ("slow release") : 5–90% by weight, preferably 10–50% by weight.

The dose is generally to be chosen so that the compounds I are present in a concentration of about 0.1–20 mg/kg of body weight of the host animal, preferably 0.5–10 mg/kg of body weight.

A. CHEMICAL EXAMPLES

Preparation instructions a)
2-(3-Chloro-2-methylph-enyl-thiomethyl)-2-imidazoline hydrochloride (56)

5.55 g (35 mmol) of 3-chloro-2-methyl-thiophenol, 5.43 g (35 mmol) of 2-chloromethyl-2-imidazoline hydrochloride and 5 g of potassium carbonate are stirred in 40 ml of ethanol at room temperature. After 25 h, the mixture is filtered and the filtrate is concentrated to dryness. The crude product is purified by column chromatography on silica gel. After the eluting agent has been stripped off, ethanolic hydrochloric acid is added to the residue and the product is precipitated by addition of ether. White crystals of melting point 208°–209° C. are obtained.

b)
1-Ethyl-2-(2,3-dimethylphenyl-aminomethyl)-2-imidazoline hydrochloride (60)

19.4 g (0.16 mol) of 2,3-dimethylaniline and 14.6 g (0.08 mol) of 1-ethyl-2-chloromethyl-2-imidazoline hydrochloride are heated under reflux in 50 ml of ethanol for 3 hours. Thereafter, the solvent is largely stripped off in vacuo, the resulting crystal sludge is filtered and the filter cake is recrystallized several times from isopropanol. Yield: 16.5 g (78% of theory) of white crystals of melting point 209°–211° C.

c)
1-n-Propyl-2-(2,3-dimethylphenyl-aminomethyl)-2-imidazoline hydrochloride (62)

4.8 g (30 mmol) of 2,3-dimethylanilino-acetonitrile, 3.4 g (33 mmol) of N-(n-propyl)-ethylenediamine and 260 mg of sodium polysulfide (Na$_2$S$_4$) are stirred together at 50° C. for 4 h. The excess amine is then stripped off under a high vacuum, ethanolic hydrochloric acid is added to the residue and the hydrochloride is precipitated by addition of ether. The crude product is purified by recrystallization from acetone/ether. 5.7 g (67%) of melting point 145°–148° C. are obtained.

d)
1-Allyl-2-(2,3-dimethylphenoxy-methyl)-2-imidazoline hydrochloride (75)

4.84 g (30 mmol) of 2,3-dimethylphenoxy-acetonitrile, 3.3 g (33 mmol) of N-allyl-ethylenediamine and 260 mg of sodium polysulfide (Na$_2$S$_4$) are stirred together at 50° C. for 4 hours. The excess amine is then stripped off under a high vacuum, ethanolic hydrochloric acid is added to the residue and the hydrochloride is precipitated by addition of ether.

The compounds of the general formula I can be prepared in accordance with these instructions.

| No. | R$^2$ | R$^3$ | R$^1$ | X | R$^4$ | R$^5$ | M.p. [°C.] |
|---|---|---|---|---|---|---|---|
| 1 | CF$_3$ | Cl | 5-Cl | NH | H | H | 288 (decomposition) |

-continued

| No. | R² | R³ | R¹ | X | R⁴ | R⁵ | M.p. [°C.] |
|---|---|---|---|---|---|---|---|
| 2 | CH₃ | Cl | 6-Cl | NH | H | H | 263–266 |
| 4 | CH₃ | Cl | 4-F | NH | H | H | 267 (decomposition) |
| 5 | CF₃ | Cl | 4-F | NH | H | H | 279–283 |
| 6 | F | Cl | 4-Cl | NH | H | H | 291 |
| 7 | CH₃ | CH₃ | 4-OCH₃ | NH | H | H | 233–237 |
| 8 | CH₃ | CH₃ | 4-CH₃ | NH | H | H | 244 |
| 19 | NO₂ | CH₃ | H | NH | H | H | 254 (decomposition) |
| 28 | —(CH₂)₄— | | H | NH | H | H | 243–246 |
| 39 | F | CH₃ | H | NH | H | H | 261 (decomposition) |
| 40 | Br | CH₃ | H | NH | H | H | 271 (decomposition) |
| 41 | Cl | F | H | NH | H | H | 267–271 |
| 49 | CH₃ | CH₃' | H | NH | CH₃ | H | 241–243 |
| 52 | CH₃ | CH₃ | H | NH | CH₃ | C₂H₅ | 148–150 |
| 56 | Cl | CH₃ | H | S | H | H | 208–209 |
| 60 | CH₃ | CH₃ | H | NH | H | C₂H₅ | 209–211 |
| 62 | CH₃ | CH₃ | H | NH | H | n-Prop | 145–148 |
| 63 | CH₃ | CH₃ | H | NH | H | i-Prop | 198 (decomposition) |
| 67 | CH₃ | CH₃ | H | NH | H | Allyl | 167–171 |
| 71 | CH₃ | CH₃ | H | NH | H | (cyclohexyl) | 70–78 |
| 75 | CH₃ | CH₃ | H | O | H | Allyl | 170–173 |
| 92 | CH₃ | CH₃ | H | NCH₃ | H | C₂H₅ | |
| 66 | Cl | Cl | H | NH | H | C₂H₅ | 284–287 |
| 73 | CH₃ | CH₃ | H | NH | H | CH₂CF₃ | 207–210 |

B. Biological Examples

Guineapigs with tick infestation are used as the test model for demonstration of a systemic ectoparasiticidal activity in animals.

For this, guineapigs sitting in plastic cylinders are infested on day d 0 with in each case 100 fasting nymphs of the brown dog tick Ripicephalus sanguineus. On day d+1, when the ticks have adhered firmly by sucking, the guineapigs are transferred to an apparatus which enables the nymphs which have let go in the fully sucked state to be collected. In the case of untreated control animals, the ticks have sucked themselves full in the course of days d+5, d+6 and d+7, let go from the host animal and can be removed from the apparatus. In general 20–50 of the 100 nymphs develop on the guineapigs under these conditions.

To test the systemic activity in animals, the guineapigs infested with ticks are injected subcutaneously with substances of the general formula I in a dosage of in each case 10 mg/kg or less on days d+1, d+2, d+3 and d+4. If the test substance has a systemic action in the animal, only a few ticks, if any, develop, in contrast to the untreated controls.

In this test, the results contained in the table were achieved with a dosage of 10 mg/kg:

| Substance No. | Number of ticks developed |
|---|---|
| 19 | 2 |
| 60 | 0 |
| 61 | 1 |
| 98 | 0 |
| 99 | 0 |
| 100 | 0 |
| 101 | 0 |
| 102 | 0 |
| 103 | 0 |
| 106 | 0 |
| 108 | 0 |

We claim:

1. A method for systemic combating of ectoparasites in host animals comprising administering parenterally, percutaneously or orally to the host animal for systemic combating of ectoparasites, an effective amount of a compound of the formula (I)

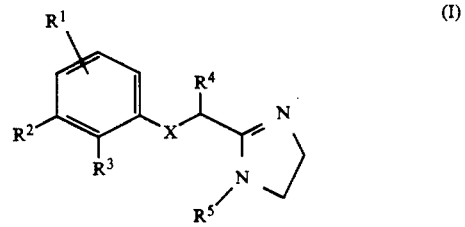

in which
$R^1$ is hydrogen, $(C_1–C_5)$-alkyl, $(C_1–C_3)$-halogenoalkyl or halogen;
$R^2$ and $R^3$ independently of one another are $(C_1–C_5)$-alkyl, $(C_2–C_5)$-alkenyl, $(C_2–C_5)$-alkynyl, $(C_3–C_7)$-cycloalkyl, $(C_3–C_7)$-cycloalkenyl, $(C_1–C_3)$-halogenoalkyl, halogen, cyano, nitro, $(C_1–C_5)$-alkoxy, $(C_1–C_3)$-akloxy-$(C_1–C_3)$-alkyl, $(C_1–C_3)$-halogenoalkoxy or $(C_1–C_3)$-alkylthio, or $R^2$ and $R^3$ together for a polymethylene chain having 2 to 5 carbon atoms;
$R^4$ is hydrogen, $(C_1–C_{10})$-alkyl $(C_2–C_5)$-alkenyl or $(C_3–C_7)$-cycloalkyl;
$R^5$ is hydrogen, $(C_1–C_{10})$-alkyl, $(C_3–C_5)$-alkenyl, $(C_3–C_5)$-alkynyl, $(C_3–C_7)$-cycloalkyl, $(C_3–C_7)$-cycloalkenyl, $(C_1–C_3)$-halogenoalkyl or $(C_1–C_3)$-alkoxy-$(C_1–C_3)$-alkyl;
X is oxygen, sulfur or an —NR⁶—group; and
$R^6$ is hydrogen, $(C_1–C_5)$-alkyl, $(C_3–C_5)$-alkenyl, $(C_3–C_5)$-alkynyl, $(C_3–C_7)$-cycloalkyl, $(C_3–C_7)$-cycloalkenyl, $(c_1–C_3)$-halogenoalkyl or $(C_1–C_3)$-alkoxy-$(C_1–C_3)$-alkyl,
or a biologically tolerated acid addition salt thereof.

2. A method for systemic combating of ectoparasites as claimed in claim 1, wherein, in formula (I), $R^1$ is hydrogen, $(C_1-C_3)$-alkyl, $(C_1-C_3)$-halogenoalkyl, F or Cl;

$R^2$ and $R^3$ independently of one another are $(C_1-C_3)$-alkyl, $(C_2-C_3)$-alkenyl, $(C_2-C_3)$-alkynyl, $(C_3-C_5)$-cycloalkyl, $(C_1-C_3)$-halogenoalkyl, halogen, cyano, nitro, $(C_1-C_3)$-alkoxy, $(C_1-C_3)$-alkoxy-$(C_1-C_2)$-alkyl, $(C_1-C_3)$-halogenoalkoxy or $(C_1-C_3)$-alkylthio, or $R^2$ and $R^3$ together form a polymethylene chain having 2 to 5 carbon atoms;

$R^4$ is hydrogen, $(C_1-C_4)$-alkyl, $(C_2-C_3)$-alkenyl or $(C_3-C_4)$-cycloalkyl;

$R^5$ is hydrogen, $(C_1-C_4)$-alkyl, $(C_3-C_4)$-alkenyl, $(C_3-C_4)$-alkynyl, $(C_3-C_6)$-cycloaklyl, $(C_3-C_5)$-cycloalkenyl, $(C_1-C_3)$-halogenoalkyl or $(C_1-C_3)$-alkoxy-$(C_1-C_2)$-alkyl;

X is oxygen or a —$NR^6$— group; and $R^6$ is hydrogen, $(C_1-C_4)$-alkyl, $(C_3-C_4)$-alkenyl, $(C_3-C_4)$-alkynyl, $(C_3-C_6)$-cycloalkyl, $(C_1-C_3)$-halogenoalkyl or $(C_1-C_3)$-alkoxy-$(C_1-C_2)$-alkyl.

* * * * *